United States Patent
Bobo, Sr. et al.

(10) Patent No.: US 10,123,723 B2
(45) Date of Patent: Nov. 13, 2018

(54) AIR LINE PROTECTION COUPLING FOR A CATHETER

(71) Applicants: InnerSpace Neuro Solutions, Inc., Tustin, CA (US); Donald Eugene Bobo, Jr., Santa Ana, CA (US)

(72) Inventors: Donald Eugene Bobo, Sr., Fountain Valley, CA (US); David Robbins Asbury, Wildomar, CA (US)

(73) Assignee: InnerSpace Neuro Solutions, Inc., Tustin, CA (US)

(*) Notice: Subject to any disclaimer, the term of this patent is extended or adjusted under 35 U.S.C. 154(b) by 652 days.

(21) Appl. No.: 14/643,997

(22) Filed: Mar. 10, 2015

(65) Prior Publication Data
US 2015/0250974 A1 Sep. 10, 2015

Related U.S. Application Data

(60) Provisional application No. 61/967,070, filed on Mar. 10, 2014.

(51) Int. Cl.
*F16L 35/00* (2006.01)
*A61B 5/097* (2006.01)
(Continued)

(52) U.S. Cl.
CPC .............. *A61B 5/097* (2013.01); *A61B 5/036* (2013.01); *A61B 5/6852* (2013.01);
(Continued)

(58) Field of Classification Search
CPC ....... A61B 5/097; A61B 5/036; A61B 5/6852; A61B 2562/0247; A61B 2562/225;
(Continued)

(56) References Cited

U.S. PATENT DOCUMENTS 2,866,453 A 12/1958 Jewett
3,445,805 A * 5/1969 McLoad ............ H01R 13/5221
285/93 X
(Continued)

FOREIGN PATENT DOCUMENTS

EP 0846472 A1 6/1998
EP 0972535 A2 1/2000
(Continued)

OTHER PUBLICATIONS

WIPO, International Preliminary Examining Authority (International Bureau), International Preliminary Report on Patentability dated Sep. 22, 2016 in International Patent Application No. PCT/US2015/019749, 8 pages.
(Continued)

*Primary Examiner* — Greg Binda
(74) *Attorney, Agent, or Firm* — Inskeep IP Group, Inc.

(57) ABSTRACT

A catheter connector has a hydrophobic end cap or washer located around the end opening to the connector's lumen. The diameter and length of the lumen below the washer is sufficiently large enough to accommodate an absorbent tubular filter that changes color when exposed to fluid. The washer acts to limit the size of the water droplet that might adhere to the end of the catheter and help maintain surface tension on the droplet to prevent it from entering the lumen. The hydrophilic tubular filter absorbs any water that might pass by the washer and thus keeps the lumen hole open.

17 Claims, 6 Drawing Sheets

(51) Int. Cl.
*A61M 39/10* (2006.01)
*A61B 5/00* (2006.01)
*A61B 5/03* (2006.01)
*A61M 5/50* (2006.01)
*A61M 39/16* (2006.01)
*A61M 39/20* (2006.01)

(52) U.S. Cl.
CPC .......... *A61M 5/5086* (2013.01); *A61M 39/10* (2013.01); *A61M 39/16* (2013.01); *A61M 39/165* (2013.01); *A61M 39/20* (2013.01); *A61B 5/031* (2013.01); *A61B 2562/0247* (2013.01); *A61B 2562/225* (2013.01); *A61M 2039/1027* (2013.01); *A61M 2205/584* (2013.01); *A61M 2205/7527* (2013.01)

(58) Field of Classification Search
CPC ..... A61B 5/031; A61M 5/5086; A61M 39/16; A61M 39/165; A61M 39/20; A61M 39/10; A61M 2039/1027; A61M 2205/7527; A61M 2205/584
USPC .......................................................... 285/93
See application file for complete search history.

(56) References Cited

U.S. PATENT DOCUMENTS

| | | | |
|---|---|---|---|
| 3,662,743 A | 5/1972 | Amarante et al. | |
| 3,714,869 A | 2/1973 | Flory et al. | |
| 3,719,070 A | 3/1973 | Hanes | |
| 3,884,242 A | 5/1975 | Bazell et al. | |
| 4,019,515 A | 4/1977 | Kornblum et al. | |
| 4,077,394 A | 3/1978 | McCurdy | |
| 4,301,811 A | 11/1981 | Layton | |
| 4,776,347 A | 10/1988 | Matthews | |
| 4,901,735 A | 2/1990 | Von Berg | |
| 4,903,707 A | 2/1990 | Knute et al. | |
| 4,934,375 A | 6/1990 | Cole et al. | |
| 5,215,529 A | 6/1993 | Fields et al. | |
| 5,279,308 A | 1/1994 | DiSabito et al. | |
| 5,573,007 A | 11/1996 | Bobo, Sr. | |
| 5,644,285 A | 7/1997 | Maurer | |
| 5,984,879 A | 11/1999 | Wallace et al. | |
| 6,231,524 B1 | 5/2001 | Wallace et al. | |
| 6,447,462 B1 | 9/2002 | Wallace et al. | |
| 7,069,788 B2 * | 7/2006 | Teugels | A61M 1/3639 |
| 7,654,967 B2 | 2/2010 | Bobo, Sr. | |
| 8,360,988 B2 | 1/2013 | Bobo, Sr. et al. | |
| 8,795,452 B2 * | 8/2014 | Alpert | A61M 39/10 |
| 2002/0151854 A1 | 10/2002 | Duchon et al. | |
| 2005/0280098 A1 | 12/2005 | Shin et al. | |
| 2007/0034906 A1 | 2/2007 | Wang et al. | |
| 2007/0208270 A1 | 9/2007 | Bobo, Sr. | |
| 2008/0157119 A1 | 7/2008 | Tsai | |
| 2010/0076410 A1 | 3/2010 | Ring | |
| 2011/0130728 A1 | 6/2011 | McKinnon | |
| 2011/0278680 A1 | 11/2011 | Tews et al. | |
| 2011/0281413 A1 | 11/2011 | Zhong et al. | |

FOREIGN PATENT DOCUMENTS

| | | |
|---|---|---|
| GB | 968376 | 9/1964 |
| GB | 2318513 A | 4/1998 |
| WO | WO2000/012003 A1 | 2/2001 |

OTHER PUBLICATIONS

WIPO, U.S. International Search Authority, International Search Report and Written Opinion dated Jun. 26, 2015 in International Patent Application No. PCT/US2015/019749, 9 pages.

WIPO, U.S. International Search Authority, International Search Report dated Jul. 27, 2001 in International Patent Application No. PCT/US2001/004749, 4 pages.

\* cited by examiner

AIR LINE PROTECTION COUPLING FOR A CATHETER

RELATED APPLICATIONS

This application claims priority to U.S. Provisional Application Ser. No. 61/967,070 filed Mar. 10, 2014 entitled Air Line Protection System, which is hereby incorporated herein by reference in its entirety.

BACKGROUND OF THE INVENTION

Presently, biologically compatible air-based pressure monitoring catheters are used in a number of medical applications to monitor pressure at various locations within a mammalian body. For example, air-based pressure monitoring catheters may be inserted into the skull of a patient thereby permitting the external monitoring of intra-cranial pressure.

Currently, a number of air-based pressure monitoring catheters have been developed. Generally, these air-based pressure monitoring catheters comprise a catheter having an air lumen formed therein which communicates with a bladder positioned at or near its distal end. In addition, the catheter includes a connector located at or near its proximal end, which may be connected to an external pressure transducer.

During use, the volume of the bladder attached to the catheter changes as pressure varies in accordance with Boyle's Law ($P_1V_1 = P_2V_2$). As a result, the pressure of the gas within the catheter becomes equal to that of the environment surrounding the bladder. The media surrounding the bladder must be capable of movement to accommodate the variations in bladder volume as pressure changes.

The use of air-based pressure monitoring catheters in low or negatively pressurized environments has proven problematic. When the proximal connector is open to atmospheric pressure in the process of periodically replacing air lost by diffusion through the bladder, the external pressure extant in the body site monitored on a bladder will expel residual air from the bladder. If the pressure is low or negative, a significant amount of residual air may remain in the bladder. The amount of air injected is intended to be sufficient to keep the bladder in an active state for a period of 8 hours. If this volume is added to the residual air in a bladder that has not been completely collapsed by the environment around it, the sum of the residual air and injected air exceed the intrinsic volume of a fully shaped bladder. Should this happen, a positive pressure is established in the bladder. The bladder is now unable to read pressure below the internal pressure created.

Air management systems such as those seen in U.S. Pub. No. 2007/0208270 and U.S. Pat. Nos. 6,447,462 and 8,360,988, which are all herein incorporated by reference, allow a user to adjust the amount of air in a system. For example, these systems allow a user to vent the air passage of the catheter to the open environment, then charge the passage with an amount of air. In this respect, the pressure in the resulting charged passage can be monitored and a pressure within the patient (e.g., within the patient's skull) can be determined.

To function properly, the air in these catheters with air-based pressure sensors must be free to move within the lumen without obstruction. If a small amount of water should get in the lumen, air is constrained from moving freely, preventing an accurate pressure reading from being determined.

SUMMARY OF THE INVENTION

One embodiment of the present invention includes a catheter connector having a hydrophobic end cap or washer located around the end opening to the connector's lumen. The diameter and length of the lumen below the washer is sufficiently large enough to accommodate an absorbent tubular filter that changes color when exposed to fluid. The washer acts to limit the size of the water droplet that might adhere to the end of the catheter and help maintain surface tension on the droplet to prevent it from entering the lumen and also prevents the tubular filter from absorbing liquid, should the proximal end contact a small pool of liquid. The hydrophilic tubular filter absorbs any water that might pass by the washer and thus keeps the lumen hole open. Additionally, by changing color, the filter can alert a user that the connector has been potentially compromised with liquid. Preferably, the connector is composed of one or more clear or transparent body components that allow a user to better see the color of the filter.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
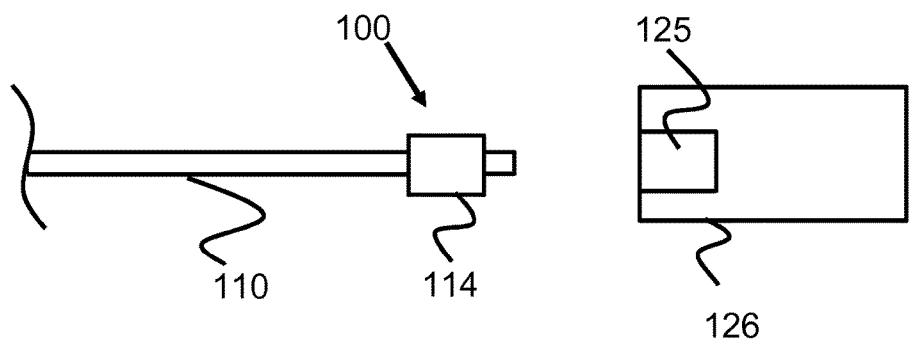
FIG. 1 illustrates a simplified, side view of one embodiment of a pressure monitoring catheter, a connector, and an air management system according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 2:
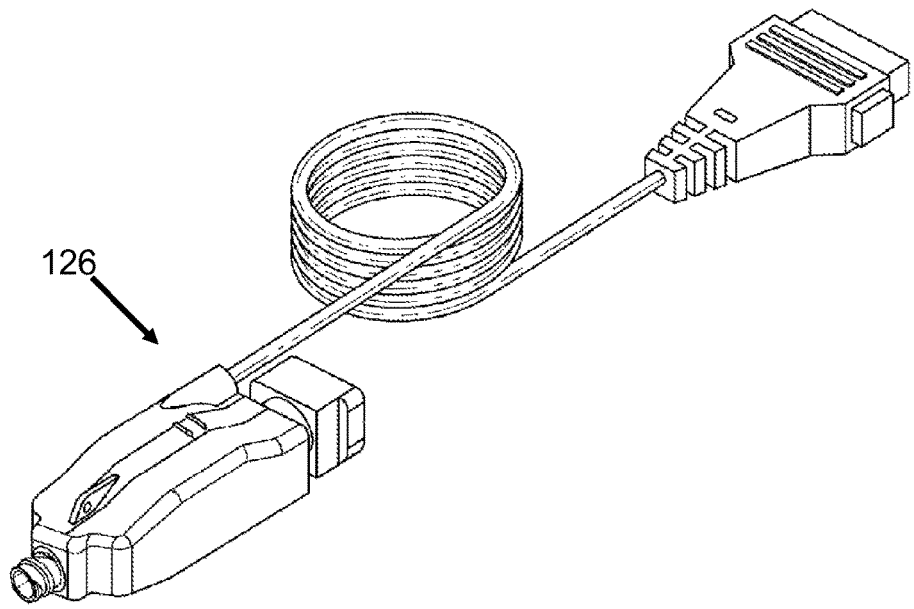
FIG. 2 illustrates a perspective view of an air management system according to the present invention.

The present invention is directed to a plug connector assembly 100 that helps prevent liquid from entering the air lumen of an air-based catheter system. As seen in FIG. 1, a catheter 110 with an air bladder is connected to one end of a male connector 114 of the connector assembly 100. The male connector 114 is sized and configured to couple with a female connector 125 of an air management system 126. In one embodiment, the air management system can be that shown in FIG. 2, which is described in greater detail in U.S. Pat. No. 8,360,988, the contents of which are hereby incorporated by reference.

Figure 3:
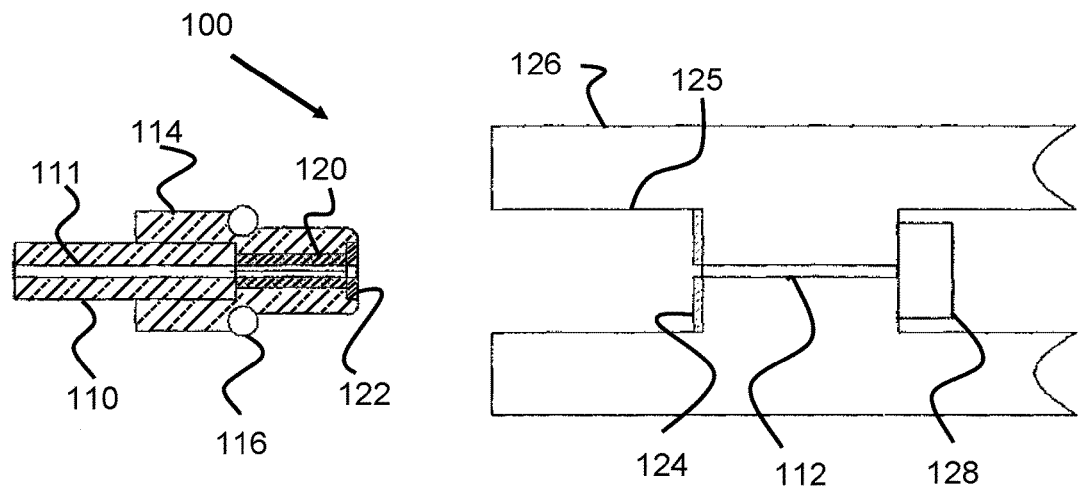
FIG. 3 illustrates a cross sectional side view of a connector for a pressure monitoring catheter.
Figure 4:
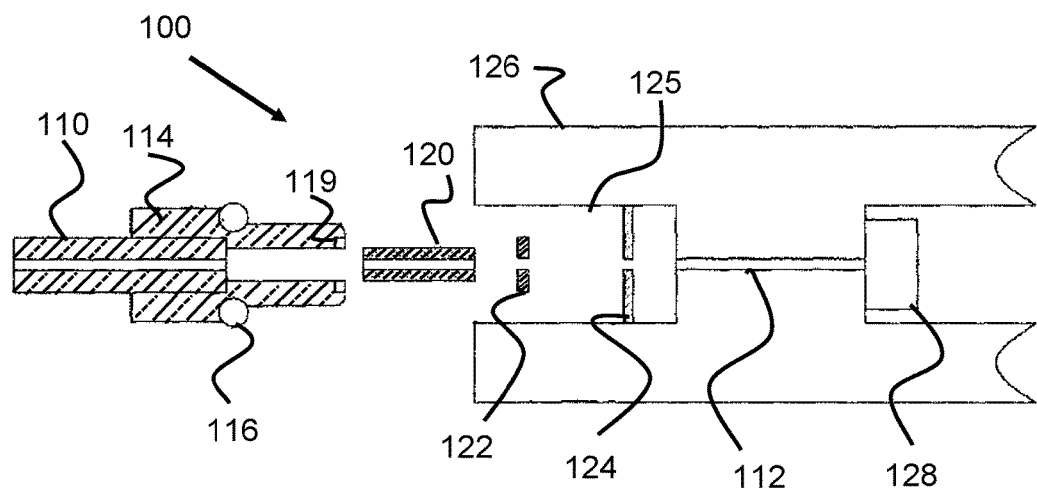
FIG. 4 illustrates an exploded cross-sectional side view of the connector of FIG. 3

As seen in FIGS. 3 and 4, a continuous passage 111 is created between the lumen of the male connector 114 and the catheter 110, terminating at the end of the male connector 114. When plugged into the female connector 125, the passage 111 connects to the passage 112 of the air management system 126, allowing a desired amount of air to be injected into the catheter 110 and allowing a pressure transducer 128 to measure changes in the air pressure within the lumens 111 and 112. The O-ring 116 on the connector 114 helps maintain the seal between the lumens 111 and 112, thereby maintaining air pressure in the system.

Figure 5:
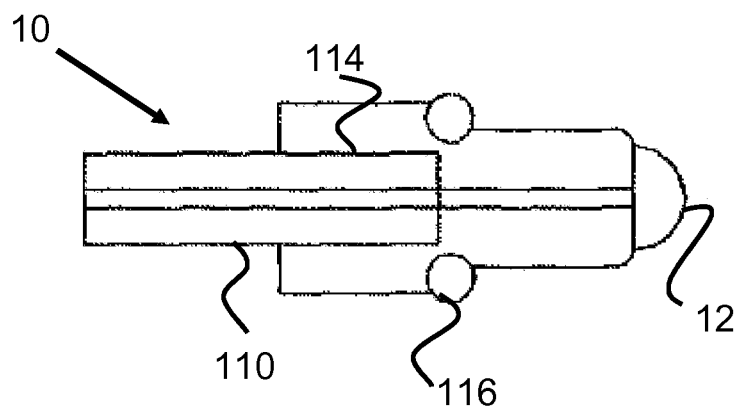
FIG. 5 illustrates a side view of the connector of FIG.3.
Figure 6:
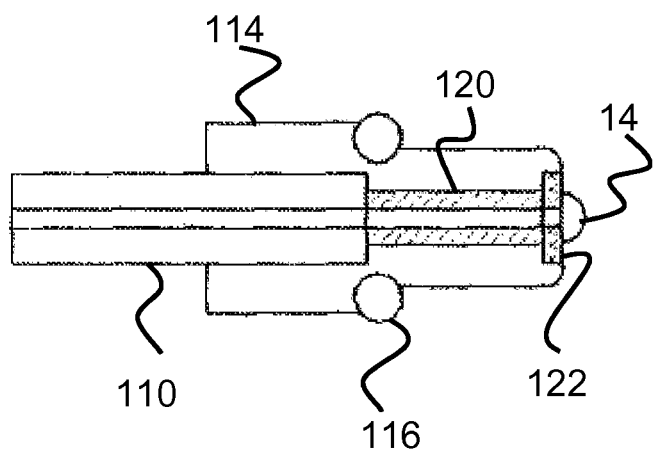
FIG. 6 illustrates a cross sectional side view of the connector of FIG. 3.

Since the lumens 111 and 112 tend to have a relatively small diameter, even small amounts of fluid can block or interfere with the free flow of air in the system, preventing the air management system 126 from accurately measuring pressure. In order to help prevent fluid into the system, the male connector 114 includes a cap or washer 122 located within an inset area 119 and which is preferably composed of a hydrophobic material. As seen in FIGS. 5 and 6, if a larger liquid droplet 12 or smaller water liquid 14 should attach itself to the end of the male connector 114, the hydrophobic material of the washer 122 helps maintain the surface tension of the droplet 12, preventing the liquid from entering the lumen 111.

The male connector 114 further includes a fluid absorbent, hydrophilic filter 120, having a tubular shape through which the lumen 111 passes through and which is located adjacent to the hydrophobic washer 122. If liquid does get pushed into the lumen 111, the filter 120 will absorb the liquid, keeping the lumen 111 clear of liquid obstruction.

The filter 120 can further act as a warning system to the user, indicating that fluid has entered the lumen 111 and that the male connector 114 has been compromised. In one embodiment, the body of the male connector 114 is composed of a clear material and the filter contains a material that changes color when exposed to water. For example, the filter 120 can contain dried, food-grade dye, such as any FD&C rated food dye, such that when contacted by liquid, the dye causes the filter 120 to change to a bright color. Since the male connector 114 is composed of a clear material, the user can clearly see the color change and therefore can replace the male connector 114 on the catheter 110.

Optionally, additional filter material 124 can be located at the end of the female connector 125, around the opening to lumen 112. Like filter 120, filter 124 can absorb liquid and can further include a color-changing substance to indicate exposure to liquid.

Figure 7:
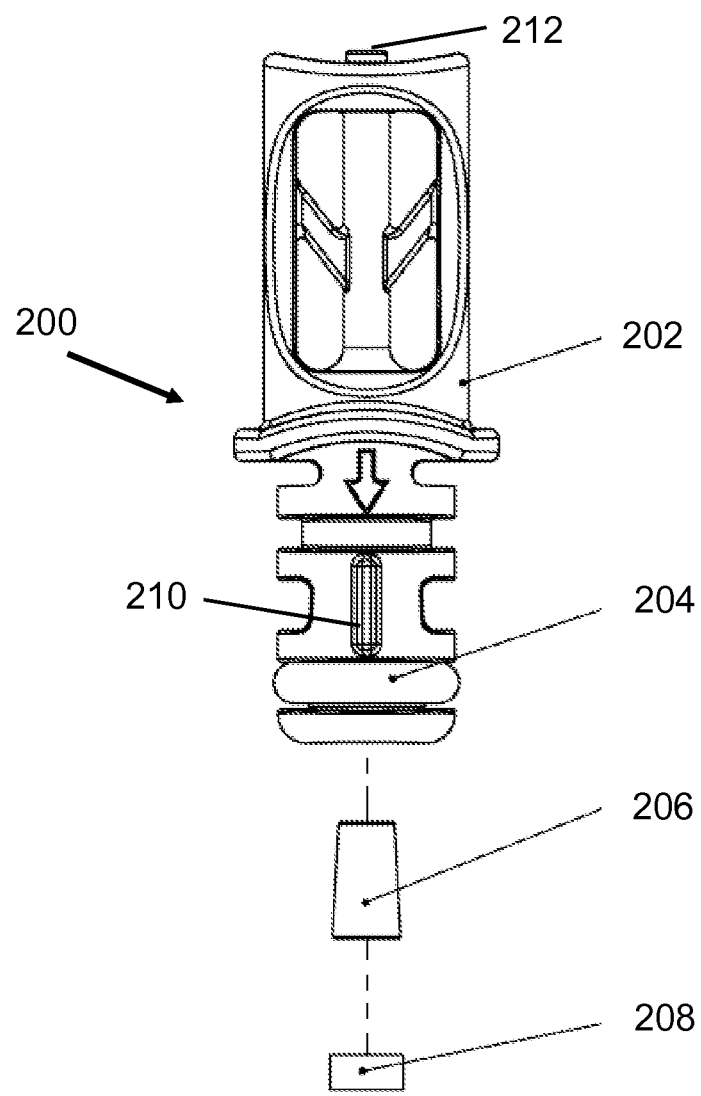
FIG. 7 illustrates an exploded view of another embodiment for a pressure monitoring catheter.
Figure 8:
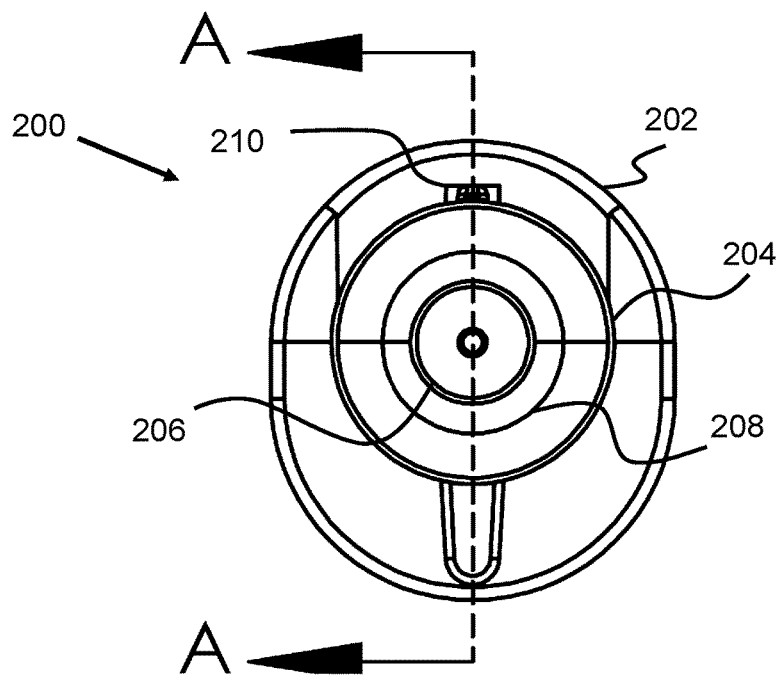
FIG. 8 illustrates an end view of the pressure monitoring catheter connector of FIG. 7.
Figure 9:
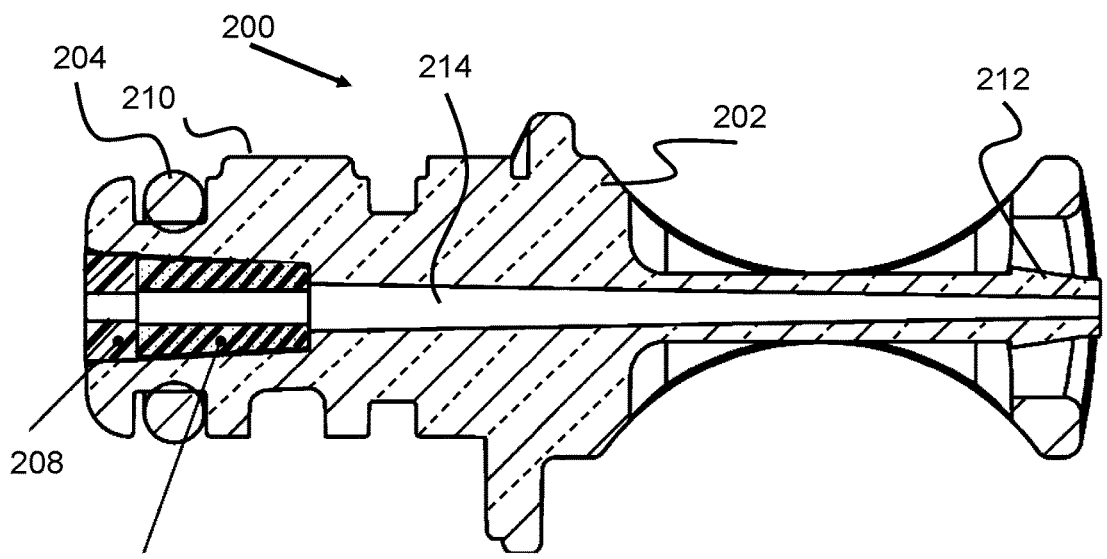
FIG. 9 illustrates a cross section side view of the pressure monitoring catheter connector in FIG. 8 along lines A.

FIGS. 7-9 illustrate another embodiment of a male connector 200 that is generally similar to the previously described connector 114. For example, the connector 200 includes a body 202, a lumen passage 214, a tubular color-changing filter 206, a hydrophobic cap/washer 208, and an o-ring 204.

Figure 10:
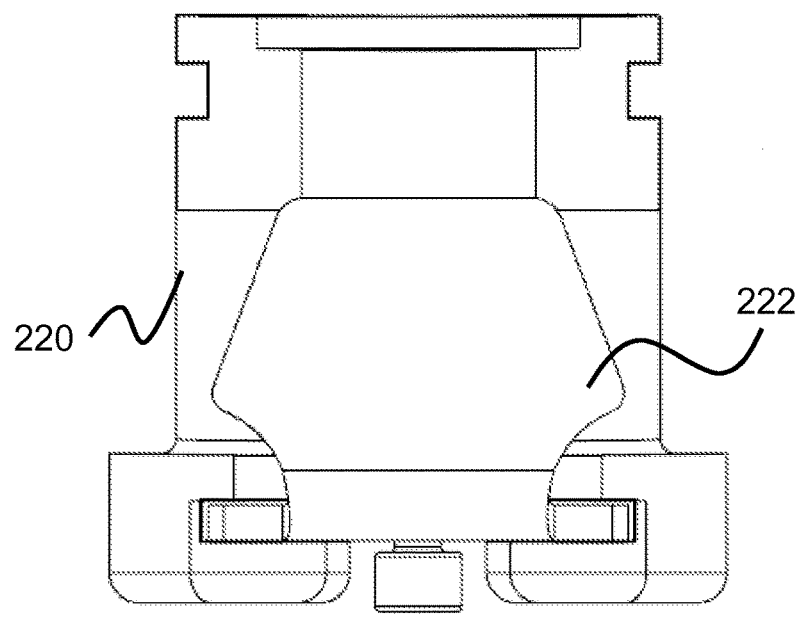
FIG. 10 illustrates a top view of a female connector used with the pressure monitoring catheter connector of FIG. 7.
Figure 11:
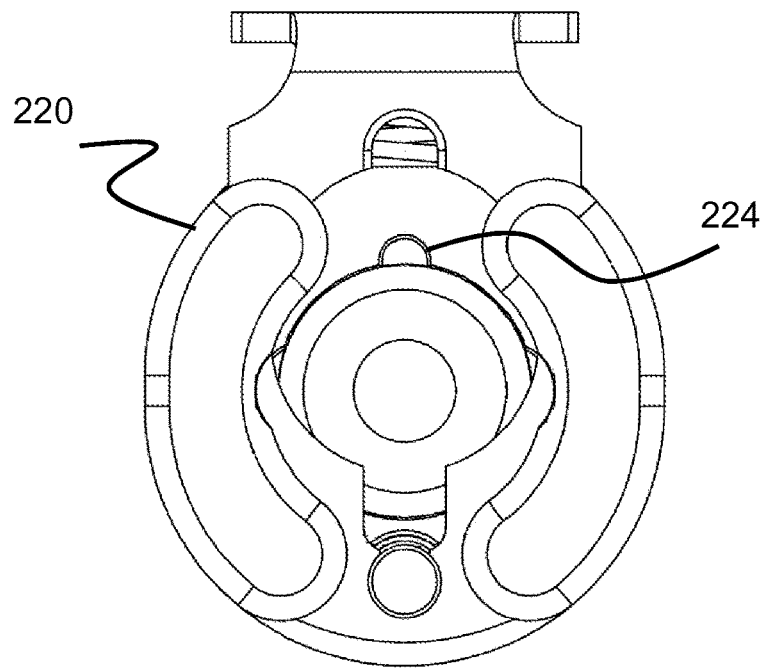
FIG.11 illustrates an end view of the female connector of FIG. 10 used with the pressure monitoring catheter connector of FIG.7.

As best seen in FIG. 9, the connector 200 also includes a barbed end portion 212 that allows easy connection and disconnection to a catheter 110. Also, a raised key region 210 aligns with a keyway 224 on the female connector 220 (FIGS. 10 and 11), allowing connection of the male connector 200 at only a single rotational orientation. By allowing only a single rotational orientation, a latch mechanism can be included, latching the male connector 200 with the female connector 220.

Since pushing the male connector 200 into the female connector 220 can inject a significant and possibly undesirable amount of air into the lumens of the catheter 110 and air management system 126, the female connector includes two venting channels 222 that allow air to escape as the male connector 200 is pushed in.

It should be understood that while the shapes and sizes of various components have been described, variations on these components are also contemplated according to the present invention. For example, while the filter member has been described as tubular, other shapes are also possible, such as a plurality of elongated, axial filter strips or a conical tube. In another example, the hydrophobic cap or washer may be generally circular, square, rectangle, or any other shape.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A connector assembly for an air-based catheter, comprising:
    a connector body having a first end, a second end, and a lumen extending between and opening at said first end and said second end; said first end being configured to connect to a catheter and said second end being configured to connect to a receptacle in communication with an air management system;
    a hydrophobic cap member located at said second end of said connector body; said hydrophobic cap member having an aperture opening to said lumen of said connector body; and
    a filter member located within said lumen near said second end opening to said lumen of said connector body;
    wherein, when said connector assembly is connected to said receptacle in communication with said air management system, a single, continuous air passage is created with said air-based catheter and said air management system.

2. The connector assembly of claim 1, wherein said filter member is a tubular shape.

3. The connector assembly of claim 1, wherein said filter member is located adjacent to said hydrophobic cap.

4. The connector assembly of claim 1, wherein said filter member contains a substance that changes color when exposed to liquid.

5. The connector assembly of claim 4, wherein said connector body is at least partially composed of a transparent material.

6. The connector assembly of claim 1, wherein said first end of said connector body includes a barb-shaped feature for connecting to a catheter.

7. The connector assembly of claim 1, further comprising a receptacle, wherein said receptacle is a female connector assembly shaped to mate with said first end of said connector body; said female connector including one or more air channels configured to vent air during connection of said connector body with said female connector.

8. A connector assembly for an air-based catheter, comprising:
a connector body having a first end, a second end, and a lumen opening at said first end and said second end; said first end being configured to connect to a catheter and said second end being configured to connect to a receptacle in communication with an air management system;
a cap member located at said second end of said connector body; said cap member having an aperture opening to said lumen of said connector body and is resistant to absorbing water; and,
a liquid absorbing member located within said lumen near said second end and opening to said lumen of said connector body;
wherein, when said connector assembly is connected to said receptacle in communication with said air management system, a single, continuous air passage is created with said air-based catheter and said air management system.

9. The connector assembly of claim 8, wherein said liquid absorbing member is in the form of a tubular shape.

10. The connector assembly of claim 8, wherein said liquid absorbing member is located adjacent to said cap member.

11. The connector assembly of claim 8, wherein said liquid absorbing member contains a substance that changes color when exposed to liquid.

12. The connector assembly of claim 11, wherein said connector body is at least partially composed of a transparent material.

13. The connector assembly of claim 8, wherein said first end of said connector body includes a barb-shaped feature for connecting to a catheter.

14. The connector assembly of claim 8, further comprising a receptacle, wherein said receptacle is a female connector assembly shaped to mate with said first end of said connector body; said female connector including one or more air channels configured to vent air during connection of said connector body with said female connector.

15. A connector assembly for an air-based catheter, comprising:
a connector body having a first end, a second end, and a lumen opening at said first end and said second end; said first end being configured to connect to a catheter and said second end being configured to connect to a receptacle in communication with an air management system; said connector body being at least partially composed of a translucent material; and,
a liquid absorbing member located within said lumen near said second end; said liquid absorbing member containing a substance that changes color when exposed to liquid and a passage therethrough opening on each end to said lumen;
wherein, when said connector body is connected to said receptacle in communication with said air management system, a single, continuous air passage is created with said air based-catheter and said air management system.

16. The connector assembly of claim 15, further comprising a cap member disposed at said second end of said connector body.

17. The connector assembly of claim 15, wherein said liquid absorbing member is a tubular shape.

* * * * *